United States Patent
Ashe

(10) Patent No.: US 6,172,499 B1
(45) Date of Patent: Jan. 9, 2001

(54) EDDY CURRENT ERROR-REDUCED AC MAGNETIC POSITION MEASUREMENT SYSTEM

(75) Inventor: Westley Ashe, Milton, VT (US)

(73) Assignee: Ascension Technology Corporation ( * ) Notice: Under 35 U.S.C. 154(b), the term of this patent shall be extended for 0 days.

(21) Appl. No.: 09/430,292

(22) Filed: Oct. 29, 1999

(51) Int. Cl.⁷ .................................................. G01B 7/00
(52) U.S. Cl. ............................ 324/207.12; 324/207.17; 324/225; 702/94
(58) Field of Search .................. 324/207.11, 207.12, 324/207.17, 225, 232, 233, 247, 262, 208; 702/94, 95

(56) References Cited

U.S. PATENT DOCUMENTS

| | | | |
|---|---|---|---|
| 3,686,564 | * 8/1972 | Mallick, Jr. et al. | 324/232 |
| 4,394,831 | 7/1983 | Egli et al. | 89/41 |
| 4,829,250 | * 5/1989 | Rotier | 324/225 |
| 4,849,692 | 7/1989 | Blood | 324/208 |
| 4,945,305 | 7/1990 | Blood | 324/207.17 |
| 5,168,222 | 12/1992 | Volsin et al. | 327/207.17 |
| 5,347,289 | * 9/1994 | Elhart | 342/448 |
| 5,640,170 | 6/1997 | Anderson | 343/895 |
| 5,767,669 | 6/1998 | Hansen et al. | 324/207.12 |

* cited by examiner

Primary Examiner—Christine Oda
Assistant Examiner—Subhash Zaveri
(74) Attorney, Agent, or Firm—H. Jay Spiegel

(57) ABSTRACT

A device is disclosed for measuring the position (location and orientation) in the six degrees of freedom of a receiving antenna with respect to a transmitting antenna utilizing multiple frequency AC magnetic signals. The transmitting component consists of two or more transmitting antenna of known location and orientation relative to one another. The transmitting antenna are driven simultaneously by an AC excitation, with each antenna occupying one or more unique positions in the frequency spectrum. The receiving antennas measure the transmitted AC magnetic field plus distortions caused by conductive metals. A computer then extracts the distortion component and removes it from the received signals providing the correct position and orientation output to a high degree of accuracy.

31 Claims, 6 Drawing Sheets

EDDY CURRENT ERROR-REDUCED AC MAGNETIC POSITION MEASUREMENT SYSTEM

BACKGROUND OF THE INVENTION

The present invention relates to devices for measuring the position of receiving antennas relative to transmitting antennas using multiple frequency magnetic fields. Particularly, though not exclusively, the disclosed devices measure position in six degrees of freedom, namely motion of translation in three coordinate directions (location) and rotational motion about three coordinate axes (orientation), location being commonly defined by X, Y, and Z linear coordinates referring to three mutually perpendicular directions and orientation being commonly described by pitch, roll, and azimuth angular coordinates about three mutually perpendicular axes usually coincident with the three mutually perpendicular directions.

As used herein "position" means location and/or orientation location.

The concept of using transmitting and receiving components with electromagnetic coupling is well known in the prior art with respect to biomechanics and computerized animation, where a subject or performer wears a number or receiver components at known strategic locations on the body, typically major arm and leg bones, shoulders, spine, hands, feet, and head. This information is then used by computing systems to precisely show the relative motions of the points in question, giving a computer generated image realistic movements. When conductive materials are present, they generate eddy current fields, which distort the received magnetic field waveform, which distorts the output of the system unless the system utilizes some distortion reducing technique.

U.S. Pat. No. 4,849,692 (Blood), U.S. Pat. No. 4,945,305 (Blood), and U.S. Pat. No. 5,640,170 (Anderson) describe the use of time domain techniques to wait for the eddy current fields to decay fully. U.S. Pat. No. 5,767,669 (Hansen and Ashe) describes a system which uses time domain techniques to measure the eddy field distortion component directly and removes it from the received signal. The disadvantage of these systems is that the receivers are quite sensitive to the low frequency (under 30 Hz) error components induced in their outputs when the sense coils are rotated in the earth's magnetic field. This motion induced component can be much larger than the component of interest when transmitter to receiver distance is large, as the transmit field falls off with the cube of distance while the Earth's field remains essentially constant. Also, since these systems use sequential time division multiplexed transmitter signals, each transmitter must be energized and sufficient time must be given for the eddy components to decay or stabilize before a receiver measurement is taken. In practice this time is on the order of 2.5 mS. Since there are generally 4 distinct transmitter states consisting of sequential energization of the X, Y, and Z coils, plus one "off" interval, these systems require approximately 10 mS to acquire a sample while maintaining reasonable eddy current distortion rejection. This translates to an effective receiver sample rate Fs of 100 hertz. Since the filters on the receivers must be designed to respond to the rapidly changing transmitter signal and must not contribute to output distortion, they are typically set at a bandwidth Fp of 2 KHz. It is thus seen that the aforementioned systems inherently do not meet the Nyquist criteria, which state that a sampled system must not have frequency components present at the sampling input which exceed one half of the sampling rate if aliasing is to be avoided. External interference signals and noise between Fs and 2 Fp are thus aliased. Of particular concern are the harmonics of the power grid, which extend from 50 Hz to beyond 1 KHz. These frequency components are aliased into the passband of the system digital lowpass filters. The aliased components are quite noticeable at bandwidths of greater than 1 Hz, beyond which the output data can and does become excessively noisy in many common environments. The narrow passband required to avoid this phenomenon results in the system having a very slow response, which is unacceptable for many applications. The noise is also increased, as the ratio of Fs/2 to Fp is typically 40:1, meaning the system samples at 100 Hz while the low pass filters pass all frequency components up to 2 KHz. A system satisfying the Nyquist criteria would need to sample at 4 KHz. Since noise is proportional to the square root of bandwidth, it can be seen that, given an equivalent set of operating parameters, the time domain eddy current compensation systems will be several times noisier than a system satisfying the Nyquist sampling criteria.

The following prior art is also known to Applicant:

U.S. Pat. No. 5,168,222 (Volsin and Monin) discloses a sequentially energized transmitter producing AC magnetic fields. Such a system will not satisfy the Nyquist criteria since the individual transmitter coils must be energized for at least 2 pi/$\omega$ seconds as dictated by claim 1(e). Such timing results in aliasing of the received signals. This system uses an in phase (I) and quadrature (q) detection scheme at a single frequency to reduce metal distortion effects. Of special interest is the q term, whose value is influenced both by the proximity of the metal and its conductivity. A metal plate of given area, thickness, and spatial position relative to the system in question will result in a particular value of the q term which is then used to correct the error in the I term due to the eddy field of the metal. By changing the thickness or composition of this plate (e.g. from aluminum to stainless steel), a different value of position will be obtained out of this system without moving either the transmitter or receiver, since the system does not attempt to correct for variations in the q term due to conductivity variations in nearby metallic structures.

U.S. Pat. No. 5,347,289 (Elhardt) discloses a system in which the detection method is independent of the amplitude of the received signal, this characteristic being achieved by using rotating magnetic field vectors. The system computes position based on timing information derived from the sensing of the rotating field vector, formed by the summation of fields at a point in space due to the sin($\omega$t) transmit axis and the cos($\omega$t) transmit axis. Mathematically, this equation is A cos($\omega$t)−B sin($\omega$t)=sqrt($A^2+B^2$)*cos($\omega$t+(tan−1 (B/A)). Since the system is concerned with the arrival of the vector at the receiver in some steady state condition, it must then also be sensitive to the steady state phase shift term given as the inverse tangent of B/A. Due to the fact that the sin($\omega$t) and cos($\omega$t) fields are not spatially co-located in both position and orientation, it is obvious that each will pass through a somewhat different region of space. If there is metal in the environment, then the received field will be distorted in amplitude by the metallic eddy currents. Since the two field components do not pass through the same space, it follows that they can and in fact do incur different amounts of eddy current distortion. This has the effect of changing the B/A ratio, and it follows that the phase term tan−1(A/B) is thus distorted. Since the timing information in the system is derived from the phase of the received field, and the phase of the received field is susceptible to distortion by metallic eddy currents, it follows that the system position output will be degraded by the presence of metal. The device described also does not correct for variations in the system response due to conductivity changes in the metal environment. Thus, changing the composition, thickness, or shape of metallic objects near the system will cause the system to output different values for position even when the receiver and transmitter positions do not change. In column 10 and FIG. 7, a system utilizing 2 frequencies is disclosed. One frequency is 11 KHz and the other 30 to 100 Hz. The low frequency component is used to provide an accurate but slow update, while the higher frequency is used to provide a less accurate but higher update rate signal. Through some undescribed methodology it appears that the goal is to combine the two outputs into one single accurate but rapid output. This system is, thus, essentially, the combination of two prior art systems using an appropriate filter to combine the two outputs into one. Such a system inherently results in nonlinearities of the output both at the beginning and end of receiver motion, as the system utilizes the more rapid but less accurate sensing means during the period of motion, but, when motion stops, must somehow transition to a different position derived from the slower but more accurate sensing means. This generally results in a period of undesirable false motion, where the position output continues to change from the less accurate value to the more accurate value during a period where the receiver is stationary.

U.S. Pat. No. 5,640,170 (Anderson) discloses a transmitter configuration using a spiral conductor pattern over a conductive ground plane in order to produce a low distortion field over the configuration. This method of reducing conductive material eddy current distortion is not related to the method disclosed in this patent.

SUMMARY OF THE INVENTION

The present invention includes the following interrelated objects, aspects and features:

(1) The present invention represents a radical departure from the prior art discussed above since it is capable of satisfying the Nyquist criteria and is thus not affected by aliasing effects and the restrictions they place on the output bandwidth and noise of the system, while also offering freedom from the negative effects on output data of eddy current distortion due to conductive materials.

(2) The present invention maintains the ability to automatically compensate for the distortion over a wide range of thickness, compositions, shapes, and locations of the conductive material. It is also immune from the effects of moving the receiver through the Earth's magnetic field. The combination of these properties creates a system of greatly increased performance over prior art systems. The system provides a more accurate and therefore more useful output over a wider variety of conductive environments, while providing a superior output signal to noise ratio, which results in increased range.

(3) The device of the present invention, in a preferred embodiment thereof, consists of a two or three axis magnetic transmitter driven by a multiple frequency source coupled with a three or two axis receiver which is sensitive to the transmitted magnetic field emanating from the aforementioned activated transmitter. Moreover, there are receiver signal processing elements which serve to convert its output to a format suitable for processing by a digital computer in conjunction with a method for processing the received signals so as to thereby develop position and orientation data.

(4) According to the invention, a device is provided for quantitatively measuring the position of receiver antennas relative to transmitter antennas comprising transmitter antennas consisting of at least two aparallel antennas to generate at least two magnetic vectors, each having a unique frequency, drive means for simultaneously or sequentially generating the magnetic vectors, receiver antennas consisting of at least two aparallel antennas to detect the multiple frequency magnetic vectors, the number of transmitter antennas times the number of receiver antennas being at least equal to the number of degrees of freedom of the desired quantitative measurement of the position of the receiver antennas relative to the transmitter antennas, means for detecting and separating amplitude components of at least two frequencies, means for correcting amplitude of received magnetic vectors using information extracted from amplitude and/or phase differences between vectors of different frequency, and computing means to quantitatively compute the relative position from the multiple frequency magnetic vectors.

Accordingly, it is a first object of the present invention to provide an eddy current error-reduced AC magnetic position measurement system.

It is a further object of the present invention to provide a device for quantitatively measuring the position of receiving antennas relative to transmitting antennas without the aforesaid disadvantages of time domain compensating systems associated with aliasing effects.

It is a further object to provide such a device which is not affected by motion of the receiver in the Earth's magnetic field.

It is a yet further object to provide a system which will compensate for the presence of certain conductive materials automatically, and without adjustments by the user.

It is a still further object to perform this compensation continuously on each cycle, such that false motion effects are avoided.

These and other objects, aspects and features of the present invention will be better understood from the following detailed description of the preferred embodiments when read in conjunction with the appended drawing figures.

BRIEF DESCRIPTION OF THE DRAWINGS

The invention will now be described, by way of example, which reference to the accompanying drawings, in which.

SPECIFIC DESCRIPTION OF THE PREFERRED EMBODIMENTS

Figure 1:
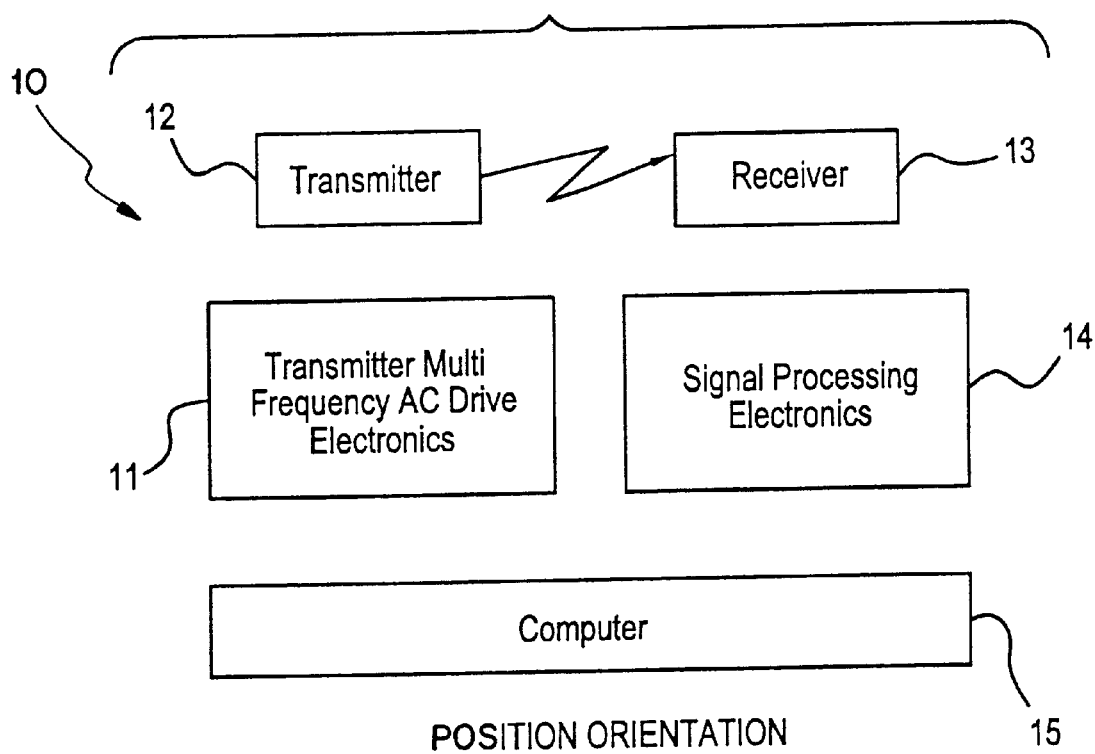
FIG. 1 shows a block diagram of the disclosed invention.
Figure 3:
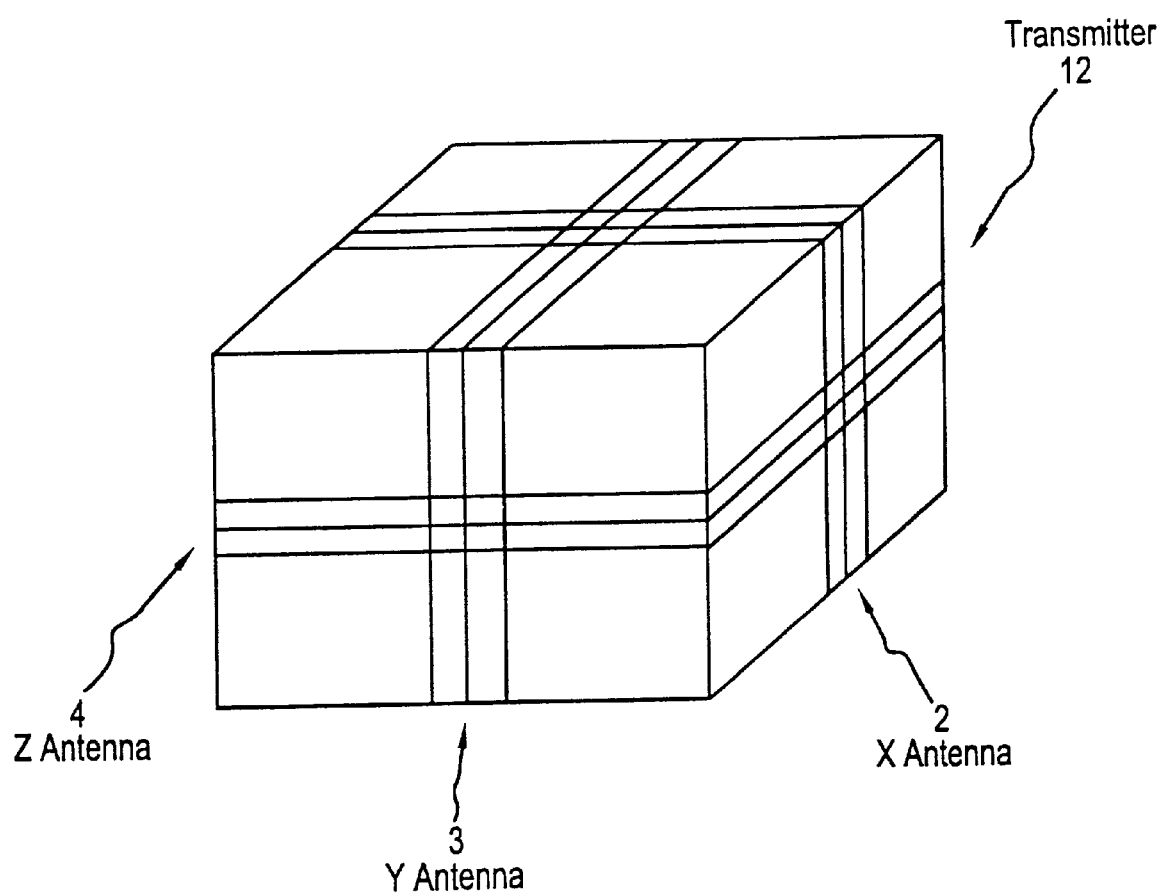
FIG. 3 shows the construction of the transmitter component of the disclosed invention.

FIG. 1 depicts the major elements of a preferred embodiment of the disclosed invention. The magnetic position (location and orientation) measuring system 10 consists of:

a transmitter driver circuit 11 for providing two or more AC current signals of known amplitude, frequency, and phase to each transmitter axis, with each axis being driven by frequencies not used simultaneously by any other axis. The frequency, phase, and current amplitude of each transmit frequency element are set and/or measured by computer 15. Transmitter 12 is usually located beneath a stage (not shown) or suspended overhead near the center of a performance area (not shown) where the person or object of interest is located. Transmitter 12 consists of two or three individual antennas 2, 3, 4 (FIG. 3) arranged mutually perpendicularly, which generate a multiplicity of AC magnetic fields which are picked up by receiver 13. Receiver 13 is mounted on points of interest on the object to be tracked. Receiver 13 consists of a single coil or three or two axes with detecting means that are sensitive to AC magnetic fields, DC magnetic fields, or a combination thereof. If desired, one or more gradient field sensors may be employed. The output of receiver 13 goes into the signal processing electronics. Signal processing electronics controls, conditions, and converts analog receiver signals into a digital format suitable for further processing by computer 15. Computer 15, by way of one of numerous techniques, such as depicted in FIG. 4, then removes the effects of eddy current distortion from the received signal and computes position using well established algorithms familiar to those skilled in the art.

Figure 2:
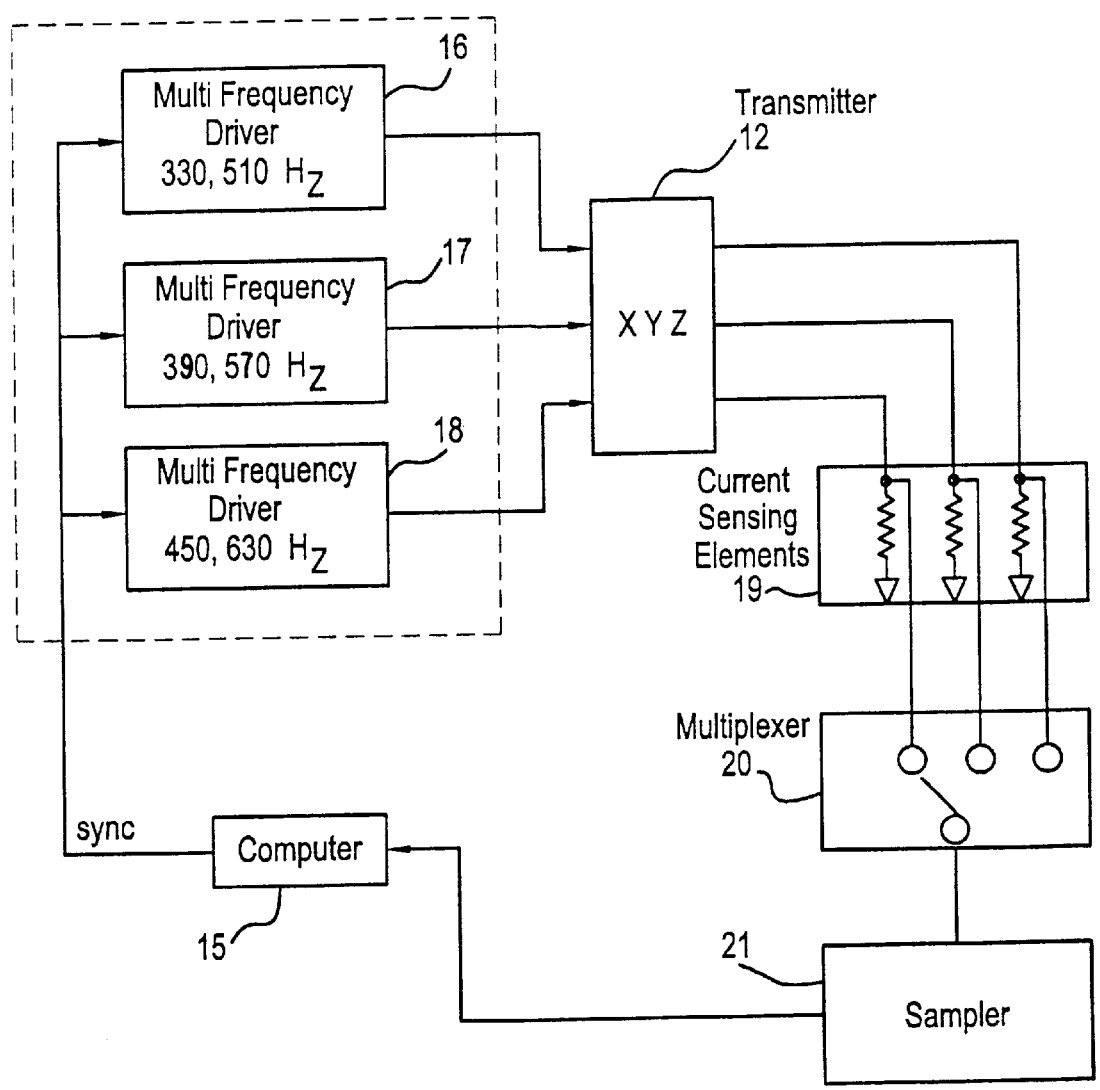
FIG. 2 shows a block diagram of the transmitter driver, which constitutes an integral part of the disclosed invention.

FIG. 2 presents details of the multiple frequency transmitter drive electronics 11. The purpose of the transmitter drive electronics 11 is to provide multiple frequency current signals to each antenna of transmitter 12, either simultaneously, or, alternately, in sequence, or, alternately, a combination thereof. It is preferred to do so simultaneously, in order to obtain maximum performance from the system. In cases where there is, for some reason, a limitation on the number of frequencies which are available or suitable for use, the total number of frequencies for the system may be reduced to no fewer than two total, and, excluding periods where the system does not transmit, at least one frequency at any instant of time is used. Multiple frequency drivers 16, 17, and 18 each produce a current waveform whose amplitude, frequency, and phase are known by computer 15. The internal schematics of these drivers are not shown as they are readily created by those familiar with electrical engineering art. Computer 15 instructs the drivers 16, 17, 18 on the number and value of frequencies to produce. The generated current waveforms are then sent through transmitter 12. Due to system tolerances related to component aging, temperature, and initial values, the amplitude of each frequency component sent through transmitter 12 by drivers 16, 17, 18 is measured by current sensor 19. The internal schematics of the current sensor 19 are not depicted as they are well known in the art. These amplitudes are then sequenced through multiplexer 20 and converted into digital signals by sampler 21. Computer 15 then uses well established signal processing algorithms to precisely determine the amplitude and phase of each frequency element produced by drivers 16, 17, 18 sent through transmitter 12, and sensed by current sensor 19. Since the magnetic field generated by a coil is related to the current waveform through the conductors of that coil, the system can precisely determine the amplitude and phase of the magnetic field output from each frequency component of each axis of transmitter 12, which is sometimes distorted to a degree by eddy current effects before being detected by receiver 13.

Figure 4:
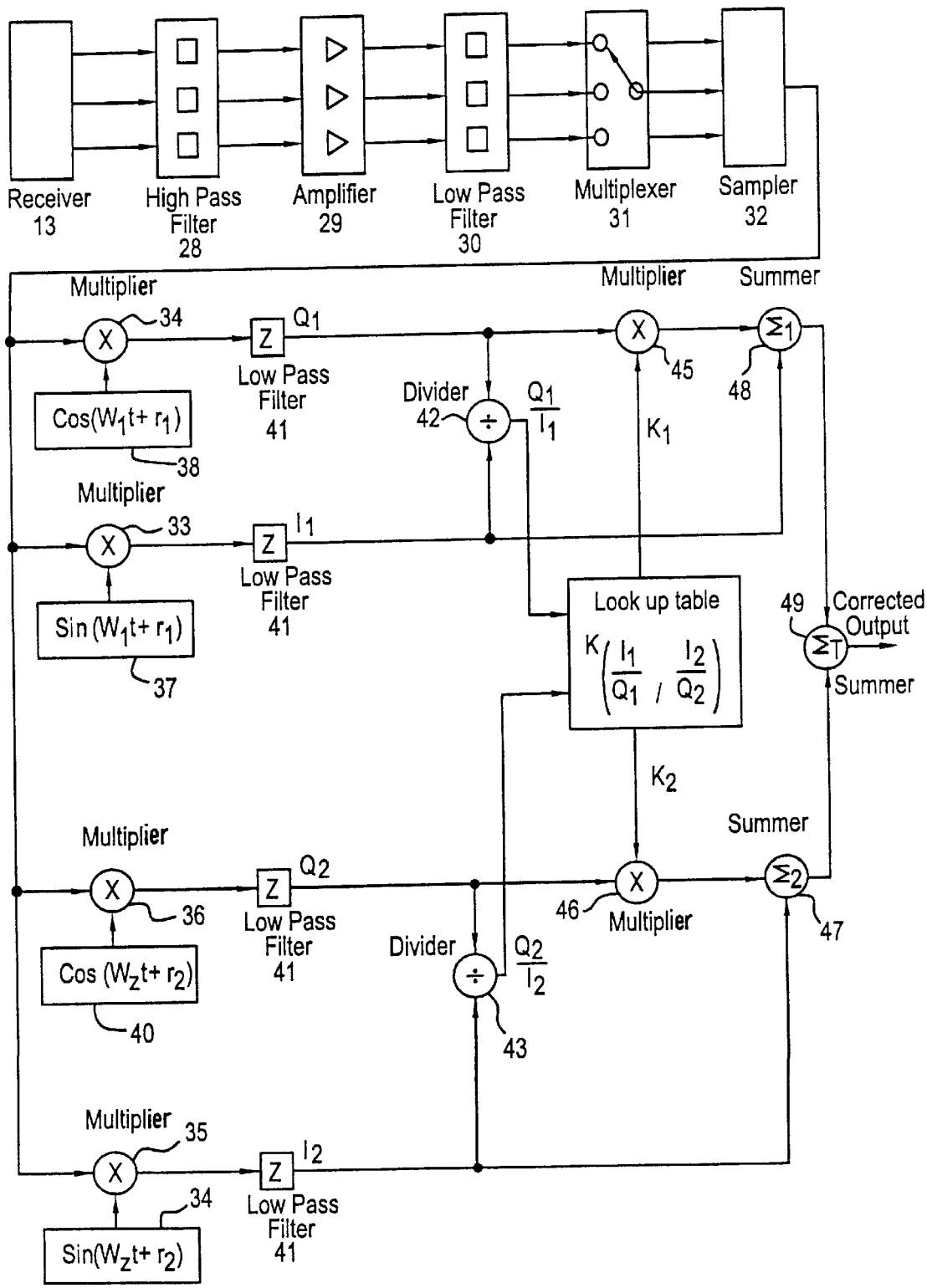
FIG. 4 shows a block diagram of the receiver signal processing technique which constitutes an integral part of the disclosed invention.

FIG. 4 shows the preferred receiver signal processing elements. Receiver 13 consists of a single coil or three or two magnetic sensors arranged approximately orthogonally with respect to each other. Each sensor means is sensitive to magnetic fields. No detailed drawing of receiver 13 is provided, as the methods to produce sensors sensitive to magnetic fields are numerous and well known to those skilled in the art. High pass filter 28 removes low frequency components under 200 Hz which result from sensor motion within the Earth's field, the stronger power line harmonics of 50, 60, 150, and 180 Hz, and low frequency noise from the sensors. These can cause saturation of amplifier 29 under certain conditions and result in systematic errors in the position output of computer 15. Amplifier 29 amplifies the signals from receiver 13 to levels suitable for further processing. Low pass filter 30 band limits the signal to a value less than one half of the cyclic sampling rate of multiplexer 31, which is required for the system to satisfy the Nyquist criteria. This action improves the performance of the system by removing frequency aliasing effects. Multiplexer 31 samples each sensor channel at a determined rate and passes the samples to sampler 32. Sampler 32 then converts the data into digital format suitable for further processing inside computer 15. It is understood that removal or modification of low pass filter 30, amplifier 29, high pass filter 28, multiplexer 31, or sampler 32 is possible without changing the fundamental eddy current compensating characteristics of the system.

For clarity of example, it is noted that the eddy current removal signal processing portion of the computation procedure performed by computer 15 is redundant by the formula N=(#Tx in system)*(#Rx axes in system), where n is the number of times computer 15 must iterate the eddy current procedure, using a different data set for each receiver/transmitter combination. This discussion will thus limit to one typical example, that of the magnetic field of the X transmit axis plus eddy current distortion as received by the X axis signal processing channel of the receiver system.

Reference generator 37 produces an output of A sin $(\omega_1 t + r_1)$. Reference generator 34 produces an output of A $\sin(\omega_2 t + r_2)$. Frequency terms $\omega_1$ and $\omega_2$ are set to the same value as $\omega_1$ and $\omega_2$ used by driver 16. Under the conditions of maximum receiver signal and no metal present, phase shift terms $r_1$ for references 37, 38 and $r_2$ for references 35 and 36 are adjusted such that the outputs of quadrature multipliers 34 and 36 are zero. This compensates for variable phase shifts in the receive circuitry. Performing this step simplifies system operation, as after calibration, the multipliers 34 and 36 output values resulting primarily from eddy current effects on the received signal. Lowpass filter 41 band limits the outputs from multipliers 33, 34, 35, 36. This removes signals which are at frequencies not of interest to the system, and reduces the noise in the system. A conductive material will possess a finite reactance term dictated by its shape and substance, this term being primarily an inductance term L and a resistance term R. We can then define an effective time constant $\tau = L/R$ for a particular shape and composition. A magnetic field at frequency F directed through a conductive object will induce eddy currents in the object having a magnitude represented as M and phase shift relative to the incident field represented as $\Theta$. Both M and $\Theta$ are related to the ratio of $F/\tau$.

The general form for the output of summer 48 Output= $ItxG/R^3 - ((M \sin(\Theta)C)/D^n) - ((M (\cos(\Theta))C)/D^n$, where: M is the magnitude of eddy current in the conductive object. Itx=transmitter current. G=coupling coefficient from transmitter to receiver, dependent on the instantaneous positional relationships of the two where R=distance from the transmitter to receiver, C is a geometry dependent coefficient of coupling from the conductive object to the receiver, the exact derivation of which is highly complex, D is the distance from the conductive object to the receiver, n is a geometry dependent exponent, the derivation of which is highly complex, dependent primarily on the eddy current loop geometry and distance from the receiver, and generally having a value of 2.5 to 3 for most systems.

$ItxG/R^3-((M\sin(\Theta)C)/D^n)$=the I term, a function of both transmitter to receiver coupling and metal distortion.

$((M\sin(\Theta)C)/D^n)$=the metal distorted portion of the I term.

$(M(\cos(\Theta)C)/D^n$=the Q term, a function of metal distortion.

$ItxG/R^3$=the Io term, which is the output of the system in the absence of metal.

The objective of this system is to remove the $(M\sin(\Theta)C)/D^n$ metal distortion value from the I term which will then result in that term being equal to $ItxG/R^3$, which is the metal free response Io of the system.

It can be seen that since the I term and Q term are taken at the same instant in time, from the same receiver coil, and the same transmitter coil, that R, Itx, M, $\Theta$, C, D, and n will be equal, as positions and relative geometries are the same for both the I and Q terms.

Since the Q term, $(M(\cos(\Theta)C)/D^n$, is available as a separate output, if a relationship can be found to equate this value with the $M\sin(\Theta)C)/D^n$ metal distortion value in the I term by the use of a suitable multiplier constant K, we can then perform $ItxG/R^3-((M\sin(\Theta)C)/D^n)+K(M(\cos(\Theta)C)/D^n)$, with $K=M\sin(\Theta)C)/D^n)/(M(\cos(\Theta)C)/D^n)$. Canceling terms, we see that $K=\sin\Theta/\cos\Theta=\tan\Theta$.

From the above, it is seen that the only remaining unknown is the determination of eddy current phase shift $\Theta$. One such method of determining $\Theta$ is to exploit the differences in frequency response of a given conductive object or group of objects with effective time constant $\tau$.

By using two or more frequencies, it is possible to determine the value of $\Theta$ for a complex environment in real time. The method involves the transmission of two or more frequencies within a band of frequencies whose optimal range is determined largely by the environmental parameters. For a system operating on a typical office environment, or on a motion capture stage, this range of frequencies is 100 to 1500 Hz. If the system is used in a medical context with smaller conductive objects in the form of surgical instruments or implants made from Titanium, this range may extend to several megahertz. Within this range, a given conductive object will exhibit unique received Q/I ratios as seen by a receiver at different transmitted frequencies. Determination of Q/I ratios at different frequency points within the optimum band allow the time constant $\tau$ of nearby conductive materials to be determined. The system performs this computation as follows. Divider 42 computes the ratio of $Q_1/I_1$ at frequency 1. Divider 43 computes the ratio of $Q_2/I_2$ at frequency 2. The two outputs are then used to determine the phase shift $\Theta$ of the environment and thus the multiplier $K_1$ and $K_2$ for $Q_1$ and $Q_2$ by way of a two dimensional lookup table 44. The appropriate $K_1$ and $K_2$ values are then multiplied by multiplier 45 and 46 and summed together with the $I_1$ and $I_2$ terms by summer 49. Summer 49 then outputs the eddy current error corrected magnitude value to the computational routines used to determine position.

Another method of determining the metallic time constant is to use only one frequency per transmit axis.

Figure 5:
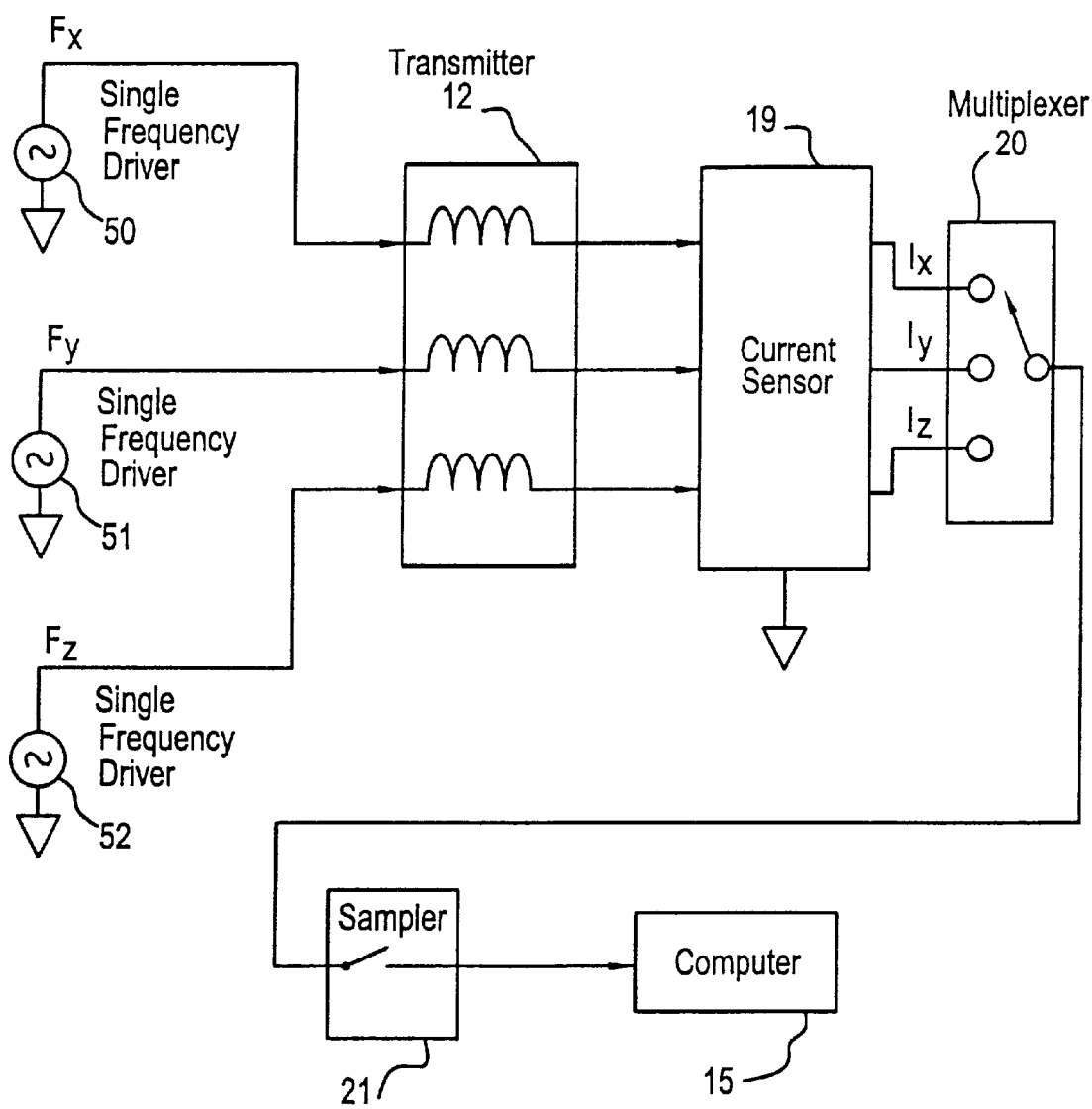
FIG. 5 shows a schematic representation of the single frequency transmitter drive electronics of the present invention.

FIG. 5 presents details of the single frequency transmitter drive electronics 50, 51, 52. The purpose of the transmitter drive electronics 50, 51, 52 is to provide single frequency current signals to each antenna of transmitter 12, with each antenna being driven at a unique frequency at a given instant of time, either simultaneously, or, alternately, in sequence, or, alternately, a combination thereof. It is generally preferred to do so simultaneously, in order to obtain maximum performance from the system. In cases where there is, for some reason, a limitation on the number of frequencies which are available or suitable for use, the total number of frequencies for the system may be reduced to no fewer than two total, and, excluding periods where the system does not transmit, at least one frequency at any instant of time is used. Single frequency drivers 50, 51, 52 produce a current waveform whose amplitude, frequency, and phase are known by computer 15. The internal schematics of these drivers are not shown as they are readily created by those familiar with the electrical engineering art. Computer 15 instructs the drivers 50, 51, 52 as to the number and value of frequencies to produce at any given instant of time. The generated current waveforms are then sent through transmitter 12. Due to system tolerances related to component aging, temperature, and initial values, the amplitude of each frequency component sent through transmitter 12 by drivers 50, 51, 52 is measured by current sensor 19. The internal schematics of the current sensor 19 are not depicted as they are well known in the art. These amplitudes are then sequenced through multiplexer 20 and converted into digital form by sampler 21. Computer 15 then uses well established signal processing algorithms to precisely determine the amplitude and phase of each frequency element produced by drivers 50, 51, 52 and sent through transmitter 12. Since the B field generated by a coil is related to the current waveform through the conductors of that coil, the system can precisely determine the amplitude and phase of the magnetic field output from each antenna of transmitter 12, which is sometimes distorted to a degree by eddy current effects before being detected by receiver 13.

Figure 6:
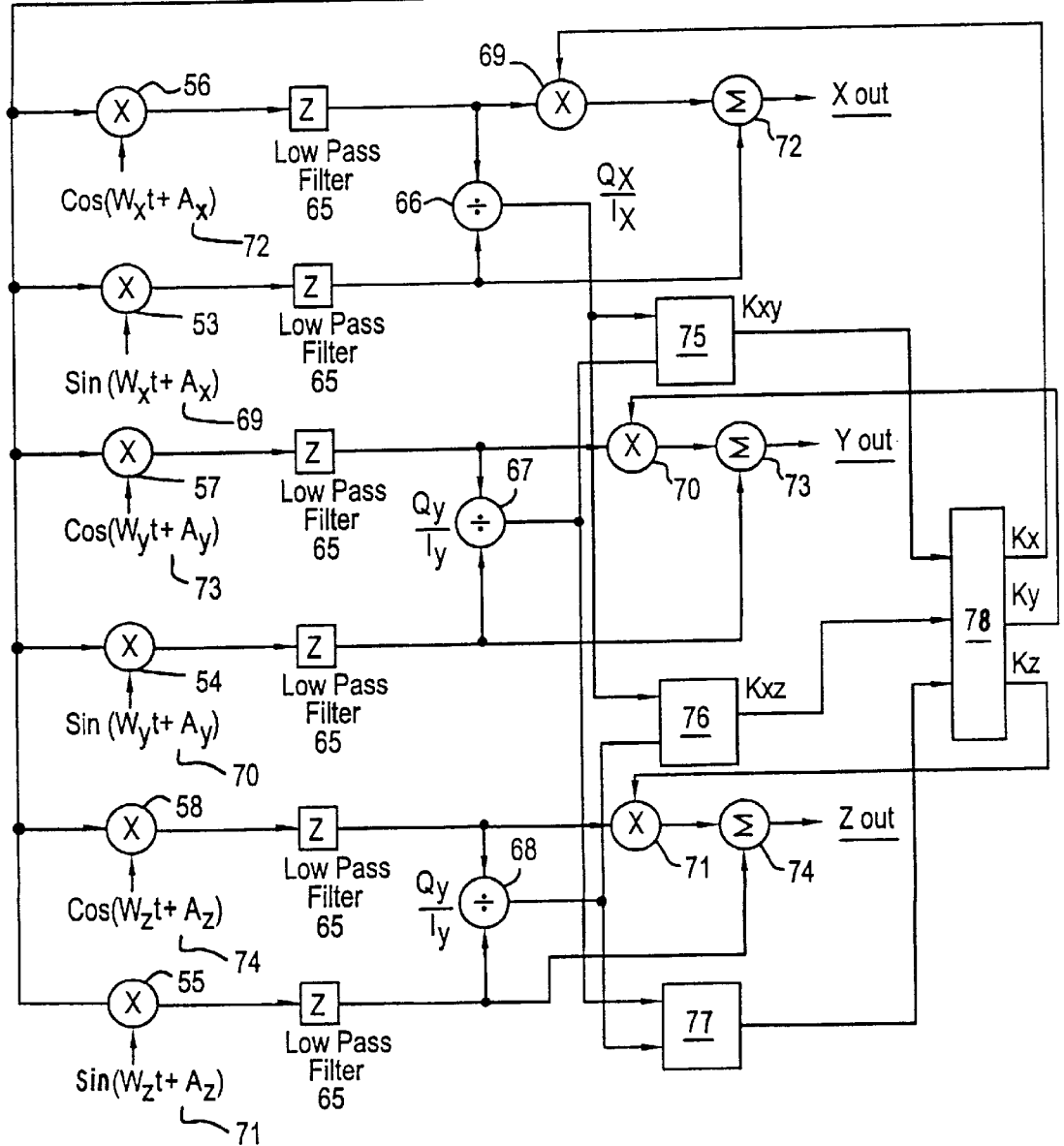
FIG. 6 shows receiver signal processing elements of an alternative embodiment of the present invention.

FIG. 6 shows the receiver signal processing elements. Receiver 13 consists of three or two magnetic sensors arranged approximately orthogonal to each other. Each sensor means is sensitive to magnetic fields. No detailed drawing of receiver 13 is provided, as the methods to produce sensors sensitive to AC magnetic fields are numerous and well known to those skilled in the art. High pass filter 28 removes low frequency components under 200 Hz which result from sensor motion within the Earth's field, the stronger power line harmonics of 50, 60, 150, and 180 Hz, and low frequency noise from the sensors. The aforementioned can cause saturation of amplifier 29 under certain conditions and result in systematic errors in the position output of computer 15. Amplifier 29 amplifies the signal from receiver 13 to levels suitable for further processing. Low pass filter 30 band limits the signal to a value less than one half of the cyclic sampling rate of multiplexer 31, which is required for the system to satisfy the Nyquist criteria. This action improves the performance of the system by removing frequency aliasing effects. Multiplexer 31 samples each sensor channel at a determined rate and passes the samples to sampler 32. Sampler 32 then converts the data into digital format suitable for further processing inside of computer 15. It is understood that removal or modification of low pass filter 30, amplifier 29, high pass filter 28, multiplexer 31, or sampler 32 is possible while still retaining a working system.

Reference generators 59, 60, 61 produce a waveform $\sin(\omega_{xt}+A_x)$, $\sin(\omega_{yt}+A_y)$, $\sin(\omega_{zt}+A_z)$. These values are multiplied with the X,Y,Z signal values from sampler 32 and the results fed into lowpass filter 65. The outputs from lowpass filter 65 are the in phase response values I of the X,Y, and Z received waveform, termed $I_x$, $I_y$, and $I_z$. The individual responses have the form $ItxG/R^3-((M\sin(\Theta)C)/D^n)$.

Reference generators 62, 63, 64 produce a waveform $\cos(\omega_{xt}+A_x)$, $\cos(\omega_{yt}+A_y)$, $\cos(\omega_{zt}+A_z)$. These values are multiplied with the X,Y,Z signal values from sampler 32 and the results fed into lowpass filter 65. The outputs from lowpass filter 65 are the quadrature response values Q of the X,Y, and Z received waveform, termed $Q_x$, $Q_y$, and $Q_z$. These outputs have the general form $Q=(M(\cos(\Theta)C)/D^n$. Since the Q term, $(M(\cos(\Theta)C)/D^n$, is available as a separate output, if a relationship can be found to equate this value with the $M\sin(\Theta)C)/D^n$ metal distortion value in the I term by the use of a suitable multiplier constant K, we can then perform $ItxG/R^3-((M\sin(\Theta)C)/D^n)+K(M(\cos(\Theta)C)/D^n)$, with $K=M\sin(\Theta)C)/D^n)/(M(\cos(\Theta)C)/D^n)$. Cancelling terms, we see that $K=\tan\Theta$. The Q components contain amplitude information and other signal criteria primarily influenced by eddy current distortion induced phase shifts in the received magnetic vectors. When there is no conductive material in the environment, the Q terms have zero value even though the I terms may be quite large.

Dividers 66, 67, 68 divide the respective Q responses by the I responses to obtain the Q/I ratio for a the X, Y and Z receiver coils. The Q/I ratio contains partial information regarding the phase shift $\Theta$ of the eddy currents in a conductive object. Computer 15 determines the phase shift $\Theta$ and thus K of the material by inputting $Q_x/I_x$, $Q_y/I_y$, and $Q_z/I_z$ into phase shift estimators 75, 76, 77. Since X,Y, and Z operate at different frequencies, the phase shift in the magnetic vector received by receiver 13 will be different at each frequency. This affects the Q/I ratio at each frequency and allows the eddy current phase shift $\Theta$ and thus multiplier K of the material to be computed by a number of well known means known to those skilled in geophysics art.

The method used in the prototype system is a two dimensional lookup table with interpolation for each combination of two axes, defined as $K_{xy}$, $K_{xz}$, and $K_{yz}$. These are depicted by 75, 76, 77, respectively, in FIG. 6. The internal operation of 75, 76, 77 is such that the Q/I ratio values for a the first subscripted coil point to a row location and the Q/I ratio for the second subscripted coil point to a column location. The aforesaid two dimensional table location contains a multiplication factor derived from the Q/I values of the two input axes. This value is then interpolated in order to avoid discontinuities of the multiplier constant K when crossing a table boundary. This interpolated value is further refined by corrector 78. Corrector 78 inputs both the I and Q signal magnitudes for each coil X,Y,Z and determines a weighting factor W to be used to combine the two possible multiplication factor outputs from 75, 76, 77 into a single factor for use in multipliers 69, 70, 71. The formulas for this are $K_x=\omega(K_{xy})+(1-\omega)K_{xz}$, $K_y=\omega(K_{xy})+(1-\omega K_{yz}$, $K_z=\omega(K_{yz})+(1-\omega)K_{xy}$. The value of weighting factor $\omega$ is, in this example, determined simply by dividing the magnitude of the Q terms of adjacent axes such that the result is less than 1. This number is then subtracted from 1 and used as the $\omega$ factor in the computations. $K_x$, $K_y$, and $K_z$ are then used to perform the operations $Q_x*K_x+I_x=Out_x$, $Q_z*K_y+I_y=Out_y$, $Q_z*K_z+I_x=Out_x$. Next, the Q/I ratio values for a the Y coil point to a row location and the Q/I ratio for the Z coil point to a column location. The aforesaid location contains a multiplier value K which is then used to perform the operation $Q_y*K_{yz}+I_z=Out_z$, where $Out_x$, $Out_y$, and $Out_z$ are eddy current distortion compensated values of the received magnetic vector from receiver 13.

The method of using only one frequency per transmitter axis has the disadvantage that the vectors produced by the different axes of transmitter 12 necessarily pass through different regions of space before being detected by receiver 13. It follows that they can and do encounter conductive materials to different extents, and that this influences the Q/I ratio obtained for a given transmitter coil. Since the correction multiplier K for a given transmitter axis is determined in part by the Q/I ratio obtained from a different transmitter axis, and since that axis may have traveled through a different extent of conductive material, the determination of multiplier K may not be totally correct for that axis. It is thus that, although simpler in hardware and requiring fewer computations, the single frequency per axis embodiment is less accurate than the multiple frequency per axis embodiment when used in a complex environment.

An important variation regarding the determination of the phase shift 8 of the environment which allows for the correct determination of multiplier K involves the use of rapid frequency changes. "Rapid" is defined as having the frequency change from a given value to another given value quickly enough so that the position of receiver 13 can be considered constant over the total interval. Using this method, the change in the in phase (I) response amplitudes at different frequencies is considered to be a result of eddy current distortion in the magnetic vector sensed by receiver 13. The phase shift $\Theta$ is then either determined by a lookup table or, given sufficient data points, a so-called nearest fit type of cross correlation can be used. In this method, computer 15 determines which phase shift $\Theta$ in the eddy current environment would reproduce the detected response. This value of $\Theta$ is then used to determine the correct scaling value for use in multiplying the I response component in order to compensate for the amplitude distortion induced by conductive eddy currents. Using this method, the Q term is unused. It is understood that the strict in-phase response component may be replaced with a more general amplitude response obtained from a peak detector or other non phase sensitive signal amplitude determination means without substantially altering the operation of the system. It is also understood that introducing a phase offset into the I term reference generator relative to the received waveform such that it is no longer strictly an in phase term would produce an output which would be used in substantially the same way. Using similar techniques, the e value may also be deduced by using only the Q terms, by way of lookup table, cross correlation, or numerous other well known methods of parameter extraction commonly used in signal processing art. One may also choose to use a combination of I and Q term ratios and values obtained over a number of frequencies by a number of well understood parameter determination means to determine a compensation multiplier or multipliers which may then be used to provide correction values by way of multiplying the aforesaid multiplier value(s) with the I terms, Q terms, or a combination thereof to produce an eddy distortion corrected value.

A third embodiment provides a significant improvement in eddy current distortion performance for many environments and contemplates adjusting the phase offsets of reference generators 34, 37 in the first embodiment or 59, 60, 61 in the second embodiment to have a slight positive value of 1 to 6 degrees. When the magnetic vectors in the frequency range of 100 to 1500 Hz encounter conductive materials commonly found in motion capture or office environments, they are amplitude reduced and positive phase shifted. This technique takes advantage of this phenomenon as the amplitude reduction of the received signal is partially offset by the improved phase alignment with the reference generator. This results in a decreased amplitude change at the output of the multiplier when conductive material is moved in and out of the environment.

It is understood that, in either the first or second embodiment, transmitter 12 may driven simultaneously, as described above, or sequentially, with information regarding in phase and/or quadrature information at a given frequency being stored for use at a later time. The transmitter 12 can then change frequency and a new set of compensation values can be computed at this later time. It is also understood that the number of frequencies is not limited to two, and, indeed, larger numbers of frequencies may be used to correct for eddy current distortion errors. It is also understood that the method used to change the frequency or frequencies output by a given transmit axis is not important. A large number of usable modulation methods exist that produce either multiple simultaneous frequencies from a given axis or time-sequenced frequencies on a given axis. These methods include sideband modulation, amplitude modulation, continuous frequency variation, and discretely stepped frequency variation. The rate at or method by which the system changes frequencies, the seperation between frequencies, and application of numerous frequency/time combinations on the various transmit axes may varied without altering the fundamental nature of the distortion correction method. The magnetic fields generated may be AC generated but this is not essential.

The inventive method may also be used to detect the presence of eddy current field distortion without attempting to correct the received values. This may be accomplished by the aforesaid means and method, but instead of correcting the received signal, the system can signal a potential error condition if certain values are computed. A simplified method is to measure the q term directly.

The present invention can also be applied to planar non-dipole configurations, single coil receivers, five degree of freedom systems and various other geometries.

As such, an invention has been disclosed in terms of apparatus and method for its practice that fulfill each and every one of the objects of the invention as set forth hereinabove and provide a new and useful eddy current error-reduced AC magnetic position measurement system of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A device for measuring the position of receiver antennas relative to transmitter antennas comprising:
   a) transmitter antenna means comprising at least two aparallel antennas adapted to generate at least two AC magnetic field vectors, said fields exhibiting at least two frequency components;
   b) receiver means comprising at least two aparallel sensors adapted to detect said AC magnetic field vectors;
   c) a first number of transmitter antennas multiplied by a second number of receiver sensors being at least equal to a total number of degrees of freedom of a desired measurement of position of the receiver means relative to the transmitter antennas;
   d) signal processing means for ascertaining magnitude of detected AC magnetic field vectors, said signal processing means computing magnitudes of at least two detected AC magnetic field vectors with relative values of phase separated components of said field vectors being employed by said signal processing means to correct detected said AC magnetic field vectors to substantially eliminate position errors caused by eddy current distortion.

2. A device according to claim 1, wherein said total number comprises at least six.

3. A device according to claim 2, wherein three transmitter antennas are arranged to produce three orthogonal pairs of AC magnetic field vectors, each said pair comprising two parallel field vectors of distinct different frequencies for a total of six vectors.

4. A device according to claim 2, comprising three receiver sensors arranged to detect said transmitted AC magnetic field vectors on three orthogonal axes.

5. A device according to claim 2, comprising two transmitter antennas arranged to produce two orthogonal pairs of AC magnetic field vectors, each said pair comprising two parallel field vectors of distinct different frequencies.

6. A device according to claim 3, including drive means for simultaneously producing said pairs of magnetic field vectors by utilizing a separate instantaneous frequency for each said vector.

7. A device according to claim 3, including drive means for producing said transmitted magnetic field vectors sequentially.

8. A device according to claim 6, wherein said drive means includes modulation means for generating sidebands in order to separate, in frequency, transmitted AC magnetic field vectors.

9. A device according to claim 7, wherein said drive means includes modulation means for generating sidebands in order to separate, in frequency, transmitted AC magnetic field vectors.

10. A device according to claim 3, wherein at least one transmit axis is driven with at least two frequencies either simultaneously or sequentially.

11. A device for measuring the position of receiver antennas relative to transmitter antennas comprising:
    a) transmitter antenna means comprising at least two aparallel antennas adapted to generate at least two AC magnetic field vectors, through frequency division multiplexing with at least two frequency components;
    b) drive means for driving each of said aparallel antennas with at least one unique frequency, said drive means driving said antennas either simultaneously or sequentially, with a different unique frequency being used for each different axis at any given instant in time;
    c) receiver means comprising at least two aparallel sensors adapted to detect said AC magnetic vectors;
    d) a first number of transmitter antennas times a second number of receiver sensors being at least equal to a total number of degrees of freedom of a desired quantitative measurement of position of a receiver sensor relative to said transmitter antennas;
    e) signal processing means for ascertaining magnitude of detected AC magnetic field vectors, said signal processing means computing the magnitudes of at least two detected AC magnetic vectors comprising at least two frequencies, with relative values of phase separated components of said vectors being used to deduce a compensation coefficient, said compensation coefficient being used to quantitatively correct said detected AC magnetic field vectors to substantially eliminate amplitude errors caused by eddy current distortion.

12. The device of claim 11, wherein said total number comprises at least six.

13. The device of claim 11, comprising three receiver sensors arranged to detect said transmitted AC magnetic field vectors on three orthogonal axes.

14. The device of claim 11, wherein said drive means includes modulation means for generating sidebands in order to separate, in frequency, transmitted AC magnetic field vectors.

15. The device of claim 11, wherein at least one transmit axis is driven with at least two frequencies either simultaneously or sequentially.

16. A method of measuring the position of receiver antennas relative to transmitter antennas including the steps of:
- a) providing transmitter antenna means comprising at least two aparellel antennas adapted to generate at least two AC magnetic field vectors, said fields exhibiting at least two frequency components;
- b) providing receiver means comprising at least two aparallel sensors adapted to detect said AC magnetic field vectors;
- c) driving said transmitter means to generate said at least two magnetic field vectors;
- d) receiving signals related to said vectors at said receiver means;
- e) providing signal processing means for ascertaining magnitude of detected signals;
- f) computing, with said signal processing means, magnitudes of at least two detected AC magnetic field vectors, relative values of phase separated components of said vectors being obtained;
- g) calculating from said relative values a compensation coefficient; and
- h) said signal processing means employing said compensation coefficient to correct vectors to compensate for eddy current distortion.

17. The method of claim 16, further including the step of driving said transmitter means to generate said at least two vectors simultaneously.

18. The method of claim 16, further including the step of driving said transmitter means to generate said at least two vectors sequentially.

19. The method of claim 16, wherein said driving step includes the step of generating sidebands to separate, in frequency, transmitted vectors.

20. A device for measuring the position of receiver antennas relative to transmitter antennas comprising:
- a) magnetic field transmitting means for transmitting magnetic field components at desired frequencies, said transmitting means transmitting a plurality of distinct frequencies;
- b) magnetic field receiving means sensitive to said transmitted field components and outputting a signal to be operated on by a signal processing means responsive to receipt of said field components;
- c) said signal processing means provided for ascertaining magnitude of detected magnetic field vectors, said signal processing means computing magnitudes of received magnetic field vectors, said magnetic field vectors comprising a plurality of frequencies, said signal processing means utilizing relative values of phase separated components of said field vectors to correct detected said magnetic field vectors to substantially eliminate errors caused by eddy current distortion.

21. The device of claim 20, wherein said transmitting means comprises a plurality of flat co-planar transmitters.

22. The device of claim 20, wherein said receiving means comprises at least one single coil receiver.

23. The device of claim 21, wherein said receiving means comprises at least one single coil receiver.

24. The device of claim 21, wherein said receiving means comprises a plurality of single coil receivers.

25. The device of claim 20, wherein said receiving means comprises at least one gradient field sensor.

26. The device of claim 25, wherein said at least one gradient field sensor comprises a plurality of gradient field sensors.

27. The device of claim 20, wherein said signal processing means includes means for calculating a compensation coefficient, said compensation coefficient being employed by said signal processing means to compensate for signal errors caused by eddy current distortion.

28. A method of measuring the position of receiver antennas relative to transmitter antennas in a space including the steps of:
- a) providing transmitter antenna means comprising at least two aparallel antennas adapted to generate at least two AC magnetic field vectors, said fields exhibiting at least two frequency components;
- b) providing receiver means comprising at least two aparallel sensors adapted to detect said AC magnetic field vectors;
- c) driving said transmitter means to generate said at least two magnetic field vectors;
- d) receiving signals related to said vectors at said receiver means;
- e) providing signal processing means for ascertaining magnitude of detected signals;
- f) computing, with said signal processing means, magnitudes of at least two detected AC magnetic field vectors, relative values of phase separated components of said vectors being obtained;
- g) determining a compensation coefficient by measuring a phase shift angle $\Theta$ of eddy currents generated by metals in or adjacent said space, said compensation coefficient comprising $\tan \Theta$; and
- h) said signal processing means employing said compensation coefficient to correct vectors to compensate for eddy current distortion.

29. The method of claim 28, further including the step of driving said transmitter means to generate said at least two vectors simultaneously.

30. The method of claim 28, further including the step of driving said transmitter means to generate said at least two vectors sequentially.

31. The method of claim 28, wherein said driving step includes the step of generating sidebands to separate, in frequency, transmitted vectors.

* * * * *